(12) United States Patent
Hu et al.

(10) Patent No.: US 10,602,778 B2
(45) Date of Patent: Mar. 31, 2020

(54) AEROSOL GENERATOR, DETACHABLE ATOMIZING DEVICE AND ELECTRONIC CIGARETTE HAVING SAME

(71) Applicant: Shenzhen First Union Technology Co., Ltd., Shenzhen, Guangdong Province (CN)

(72) Inventors: Shuyun Hu, Shenzhen (CN); Zhongli Xu, Shenzhen (CN); Yonghai Li, Shenzhen (CN)

(73) Assignee: Shenzhen First Union Technology Co., Ltd. (CN)

( * ) Notice: Subject to any disclaimer, the term of this patent is extended or adjusted under 35 U.S.C. 154(b) by 172 days.

(21) Appl. No.: 15/821,732

(22) Filed: Nov. 22, 2017

(65) Prior Publication Data

US 2018/0140018 A1    May 24, 2018

(30) Foreign Application Priority Data

Nov. 23, 2016 (CN) .......................... 2016 1 1038806

(51) Int. Cl.
*A24F 47/00* (2020.01)
*H05B 3/44* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .................................................... A24F 47/008
See application file for complete search history.

(56) References Cited

U.S. PATENT DOCUMENTS 5,369,723 A  * 11/1994 Counts .................. H05B 3/145
                                                              392/386
5,408,574 A  *  4/1995 Deevi .................. A24F 47/008
                                                              128/202.21
(Continued)

FOREIGN PATENT DOCUMENTS

CN         205456070 U     8/2016
EP         3210641 A1      8/2017
WO         2012134117 A2  10/2012

*Primary Examiner* — James Harvey
(74) *Attorney, Agent, or Firm* — PROI Intellectual Property US (57) ABSTRACT

The present invention discloses an aerosol generator, an electronic cigarette, and a detachable atomizing device. The aerosol generator includes a housing, a storage chamber, a heating device, and an aerosol discharging channel. The storage chamber is formed in the housing and configured for storing an aerosol forming substance. The heating device is disposed in the housing and configured for heating the aerosol forming substance to generate aerosol. The aerosol discharging channel is configured for discharging aerosol generated by the aerosol forming substance to the outside of the housing. The heating device includes a quartz glass body and a heating element. The heating element is encapsulated inside the quartz glass body, and the heating element is capable of generating thermal radiation and infrared radiation outwardly through the quartz glass body to heat the aerosol forming substance.

18 Claims, 8 Drawing Sheets

(51) Int. Cl.
*A61M 11/04* (2006.01)
*A61M 15/06* (2006.01)
(52) U.S. Cl.
CPC ......... *H05B 3/44* (2013.01); *A61M 2205/368* (2013.01); *H05B 2203/032* (2013.01)

(56) References Cited

U.S. PATENT DOCUMENTS

| | | | | |
|---|---|---|---|---|
| 5,468,936 | A * | 11/1995 | Deevi | H05B 3/141 219/543 |
| 5,498,855 | A * | 3/1996 | Deevi | A24F 47/008 131/194 |
| 5,530,225 | A * | 6/1996 | Hajaligol | A24F 47/008 131/194 |
| 5,665,262 | A * | 9/1997 | Hajaligol | A24F 47/008 219/553 |
| 5,878,752 | A * | 3/1999 | Adams | A24F 47/008 131/329 |
| 10,201,189 | B1 * | 2/2019 | Qiu | A24F 47/008 |
| 2013/0298905 | A1 * | 11/2013 | Levin | A24F 47/008 128/202.21 |
| 2018/0035721 | A1 * | 2/2018 | Cyphert | A24D 3/048 |
| 2018/0140018 | A1 * | 5/2018 | Hu | H05B 3/44 |
| 2018/0200458 | A1 * | 7/2018 | Li | A61M 11/042 |

* cited by examiner

AEROSOL GENERATOR, DETACHABLE ATOMIZING DEVICE AND ELECTRONIC CIGARETTE HAVING SAME

CROSS REFERENCE TO RELATED APPLICATIONS

The present application claims priority to Chinese patent application CN 2016 110 388 06.5 filed on Nov. 23, 2016.

TECHNICAL FIELD

The present invention relates to the field of electronic cigarettes, and more particularly to an aerosol generator, an electronic cigarette, and a detachable atomizing device.

BACKGROUND

At present, atomizing devices used in electronic cigarettes are atomized by means of electric heating, and conveys tobacco liquid to a heating element through a fiber or microporous liquid guiding body to be atomized and form aerosol. In the atomizing device structure disclosed in the prior art, the heating element is made of a metal material, such as a metal heating wire or a heating sheet, and the heating element directly contacts with the tobacco liquid through a fiber or microporous liquid guiding body. During the heating process, the heating element may be oxidized. The harmful substances such as metal ions or metal oxide ions generated by the heating element will migrate into the tobacco liquid, and these harmful substances will be absorbed into the body along with the aerosol when the tobacco liquid is atomized, which will affect the health of the user. At the same time, the heating element made of the metal alloy will decrease in heat transfer efficiency with oxidation, resulting in low thermal efficiency.

SUMMARY

The technical problem to be solved by the present invention is to overcome the shortcomings of the prior art and to provide an aerosol generator, an electronic cigarette, and a detachable atomizing device with high safety and high thermal efficiency.

In order to solve the above technical problem, the basic technical solution adopted by the present invention is as follows. The present invention provides an aerosol generator, comprising: a housing; a storage chamber formed in the housing and configured for storing an aerosol forming substance; a heating device disposed in the housing and configured to heat the aerosol forming substance to generate aerosol; and an aerosol discharging channel configured for discharging aerosol generated by the aerosol forming substance to the outside of the housing; wherein the heating device includes a quartz glass body and a heating element, the heating element is encapsulated inside the quartz glass body, and the heating element is capable of generating thermal radiation and infrared radiation outwardly through the quartz glass body to heat the aerosol forming substance.

Further, an expansion chamber is formed inside the quartz glass body during the encapsulating process, and a pressure discharging hole is provided in the quartz glass body to allow the expansion chamber to communicate with the outside.

Further, the heating device further includes an electrode part connected to the heating element, and at least a part of the electrode part protrudes to the outside of the quartz glass body.

Preferably, the heating element is an electric heating sheet, an electric heating wire or an electric heating net embedded in the quartz glass body.

In particular, the aerosol forming substance is solid tobacco material or tobacco liquid in a fluid form.

As an embodiment in the solution of the present invention, when the aerosol forming substance is tobacco liquid, the aerosol generator further includes a porous member, the porous member is configured for slowly conveying the tobacco liquid from the storage chamber to the heating device, and the porous member is in contact with the outer surface of the quartz glass body.

Preferably, the porous member is a microporous ceramic body, a fiber cotton, or a foam metal.

Further, both the porous member and the quartz glass body are disposed along an axial direction of the aerosol discharging channel, the porous member and the quartz glass body cooperatively define an air flow channel therebetween, and the air flow channel is in communication with the aerosol discharging channel.

As an embodiment, the porous member is disposed around the periphery of the quartz glass body, the porous member defines a plurality of axially extending air flow grooves in the inner wall, and the air flow grooves and the outer wall of the quartz glass body cooperate to form the air flow channel.

As another embodiment, the porous member is disposed around the periphery of the quartz glass body, the quartz glass body defines a plurality of axially extending air flow grooves in the outer wall, the air flow grooves are circumferentially spaced along the outer wall of the quartz glass body, and the air flow grooves and the inner wall of the porous member cooperate to form the air flow channel.

Further, the aerosol generator further includes a support for fixing the porous member and the heating device outside the porous member, wherein a liquid guiding hole is defined on the side wall of the support, through which the tobacco liquid in the storage chamber flows to the porous member.

Preferably, the quartz glass body includes a tapered portion at the top thereof so that the tobacco liquid formed by condensation in the aerosol discharging channel flows back to the outside of the heating device along the tapered portion and continues to be heated and atomized.

Further, the aerosol generator further includes an isolating cover body and a spring located at the periphery of the porous element and the heating device, wherein the isolating cover body and the spring are movably disposed in the storage chamber, and a suction nozzle cover screwed to the isolating cover body is further mounted on the housing; when the suction nozzle cover is unscrewed, the isolating cover body moves downward under the action of the spring to isolate the tobacco liquid from flowing into the porous element, and when the suction nozzle cover is screwed, the isolating cover body moves upward to allow the porous member to come into contact with the tobacco liquid.

Further, an air inlet is defined downstream of the heating device, the aerosol generator further includes an adjusting ring mounted at the position of the housing corresponding to the air inlet, and the adjusting ring is configured for adjusting the size of the air inlet.

Preferably, the quartz glass body has a cylindrical shape, a square shape or a sheet shape.

The present invention further provides an atomizing device detachably mounted inside an aerosol generator, comprising: a heating device configured for heating tobacco liquid to evaporate and generate aerosol, wherein the heating device includes a quartz glass body and a heating element, the heating element is encapsulated inside the quartz glass body, and the heating element is capable of generating thermal radiation and infrared radiation outwardly through the quartz glass body to heat the tobacco liquid; a porous member in contact with the quartz glass body of the heating device and configured for absorbing and conducting the tobacco liquid to the heating device; and a support disposed on the periphery of the heating device and the porous member, the support being configured for fixing the heating device and the porous member.

The present invention further provides an electronic cigarette, comprising an aerosol generator and a power supply device, wherein the aerosol generator may be the aerosol generator involved in the various preferred solutions described above, and the power supply device is electrically connected with the heating element of the heating device.

The beneficial effect of the present invention is as follows. The heating device involved in the present invention includes a quartz glass body and a heating body. The heating body is encapsulated inside the quartz glass. Since the quartz glass body has a lower thermal expansion coefficient than the metal heating body and is resistant to high temperature, it is suitable for the heating situation of the aerosol forming substance (tobacco or tobacco liquid), and it is safe and will not generate harmful substances. Because the quartz glass body can filter visible light and can transmit far infrared light, the heating device of the present invention can emit infrared light during operation. The quartz glass body encapsulated outside is in direct contact with the aerosol forming substance or the porous material. The aerosol forming substance is heated and atomized in a manner of combining heat radiation and infrared wave radiation with a high thermal efficiency.

DETAILED DESCRIPTION

The present invention provides an aerosol generator suitable for use with an electronic cigarette appliance which includes a heating device therein. The aerosol generator uses the heating device to heat the aerosol forming substance during its operation, and generate aerosol which may be smoked by consumers through evaporation or carbonization. The aerosol forming substance described above is solid tobacco material or tobacco liquid in a fluid form. For example, the solid tobacco material may be a traditional cigarette, a tobacco particle, or a special tobacco product, etc. The heating device is disposed directly in the storage chamber for containing solid tobacco material to heat the solid tobacco material.

As described above, the aerosol forming substance may also be a tobacco liquid made by extracting tobacco raw material and then adding other aromatic components. The tobacco liquid in a fluid form is taken as an example. The structure of the atomizing device of the aerosol generator, an electronic cigarette, and a detachable atomizing device provided in the present invention in aerosol generator and the principle of using the same will further elaborated below.

A First Embodiment

Figure 1:
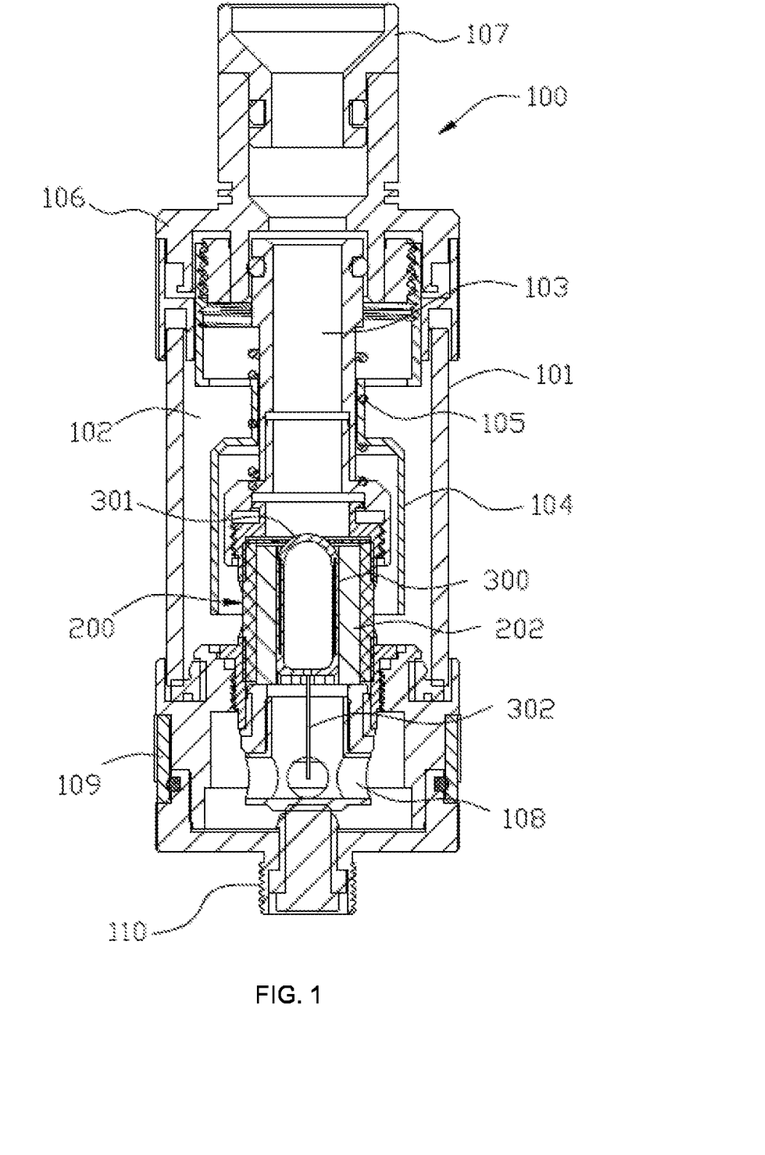
FIG. 1 is a schematic structural diagram of an aerosol generator provided in a first embodiment.

As shown in FIG. 1, the present embodiment provides an aerosol generator 100, which includes a housing 101, a storage chamber 102 disposed inside the housing 101, an atomizing device 200, and an aerosol discharging channel 103. The aerosol discharging channel 103 is formed by a vent pipe located inside the housing 101, and the space between the vent pipe and the housing 101 forms the above storage chamber 102 configured for storing tobacco liquid. The atomizing device 200 includes a heating device 300 for heating the atomized tobacco liquid. The detailed description of the heating device 300 is shown below. The heating device 300 is located downstream of the aerosol discharging channel 103, and a suction nozzle 107 is disposed upstream of the aerosol discharging channel 103 for the consumer sucking the generated aerosol.

A suction nozzle cover 106 is mounted on the upper end of the housing 101. The suction nozzle 107 is located on the suction nozzle cover 106. The suction nozzle cover 106 is configured for sealing the upper end of the storage chamber 102. When the suction nozzle cover 106 is unscrewed, tobacco liquid may be added to the storage chamber 102. A conductive connecting portion 110 is provided at the lower end of the housing 101, and the conductive connecting portion 110 is configured for connecting an external power supply device and supplying current to the heating device 300 described above.

A plurality of air inlets 108 are provided downstream of the heating device 300. An adjusting ring 109 is mounted at the position of the housing 101 corresponding to the air inlet 108, and the adjusting ring is configured for adjusting the size of the air inlet 108. When inhaling, external air enters the atomizing device 200 through the air inlet 108. The air flow can carry the generated aerosol into the aerosol discharging channel 103 when passing through the heating device 300.

Figure 2:
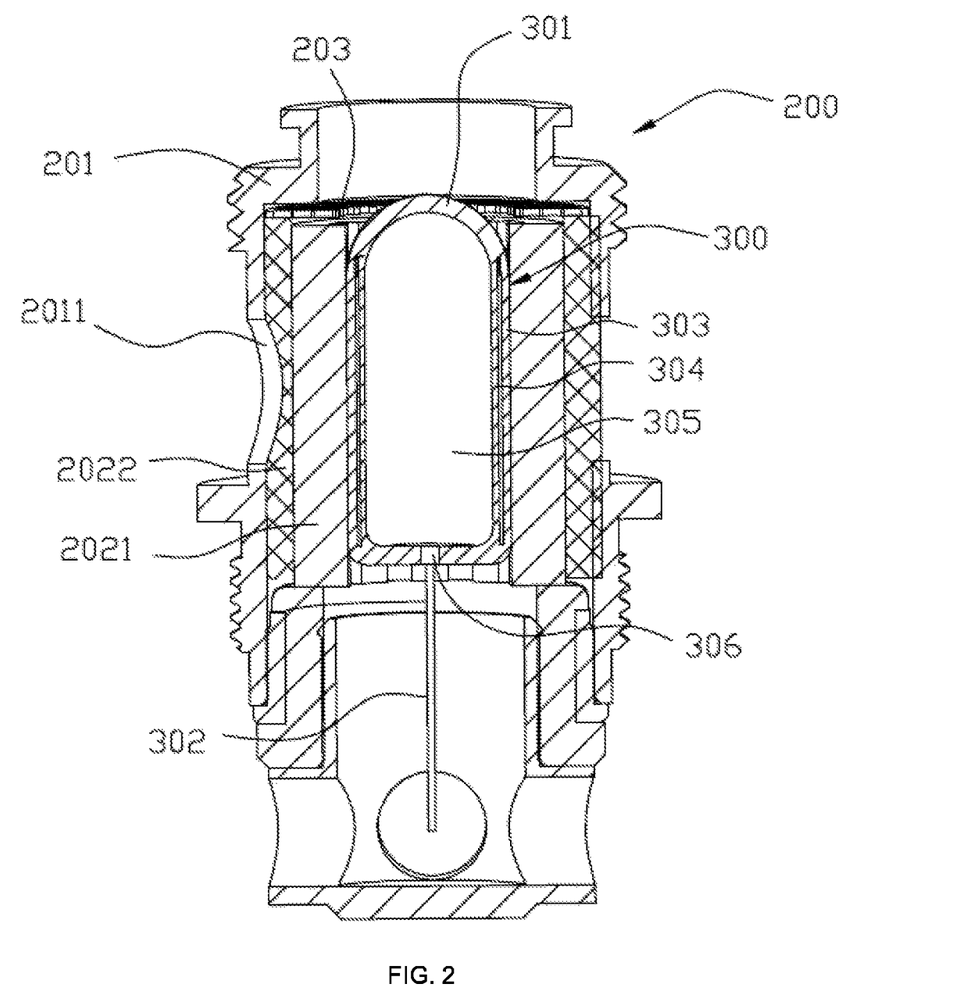
FIG. 2 is an axial cross-sectional view of an atomizing unit detachably mounted inside the aerosol generator according to a first embodiment.
Figure 3:
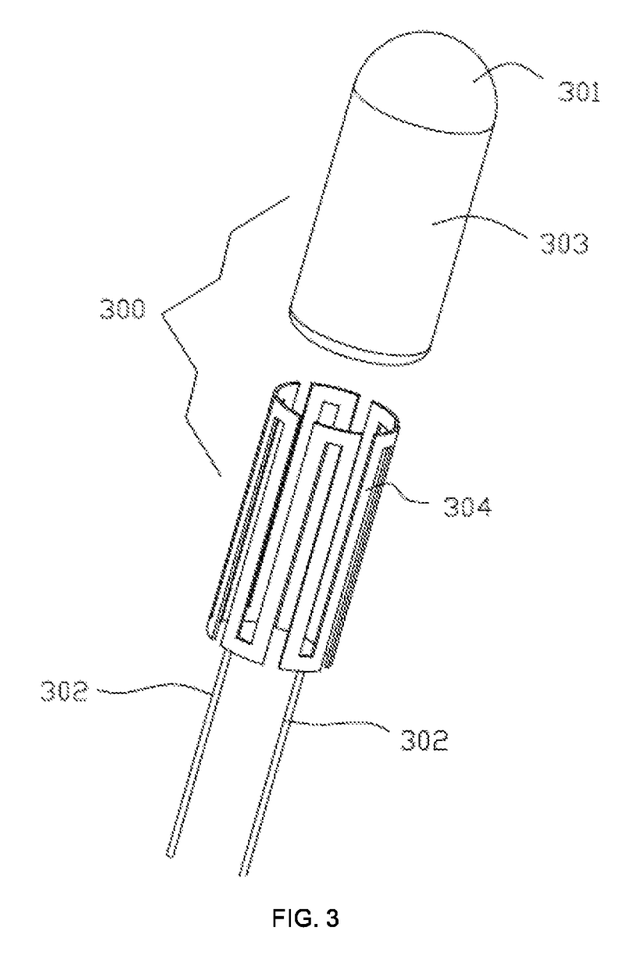
FIG. 3 is an exploded schematic view of a heating device according to a first embodiment.

As shown in conjunction with FIG. 2 and FIG. 3, the specific structure of the atomizing unit 200 described above and the heating device 300 therein is shown. In the present embodiment, the heating device 300 includes a quartz glass body 303 and a heating element 304, and the heating element 304 is encapsulated inside the quartz glass body 303. The quartz glass body 303 is resistant to high temperature, has stable chemical property, and will not generate harmful substances. In addition, due to the special internal microscopic molecular structure of quartz glass, the quartz glass body may filter visible light and may transmit far-infrared light. Therefore, the heating element 304 is capable of generating thermal radiation and infrared radiation outwardly through the quartz glass body 303 simultaneously to heat the tobacco liquid so that the tobacco liquid is evaporated to form aerosol. The thermal efficiency is higher than that of the existing simple metal heating element.

The heat-generating body 304 may also be made of a metal alloy, such as a nickel-chromium alloy. The specific shape of the heat-generating body 304 may be an electric heating sheet, an electric heating wire or an electric heating net embedded in the quartz glass body 303. In the present embodiment, a tubular electric heating sheet is preferably formed. The electric heating sheet may be formed by bending, or may be die-cut or etched and hollowed to form a fixed pattern, for example, forming a pattern as shown in FIG. 3, which includes a plurality of spaced-apart and end-to end heating elements.

In the manufacture of the heating device 300, the heating element 304 is first positioned in a specific mold, and then the fused silica glass is injected into the mold to encapsulate the heating element 304 therein. Since the heating element 304 is encapsulated, during the heating process, the tobacco liquid only contacts with the outer surface of the quartz glass body 303 and cannot contact with the heating element 304 therein. Therefore, the heating element 304 will not generate oxide ions or metal ions to enter the tobacco liquid, thus greatly improving the health and safety of smokers.

As a preferred solution in the present embodiment, an expansion chamber 305 is formed inside the quartz glass body 303 during the encapsulating process, and a pressure discharging hole 306 is provided in the quartz glass body 303 to allow the expansion chamber 305 to communicate with the outside. The pressure discharging hole 306 is disposed at the bottom of the quartz glass body 303 so that the tobacco liquid will not flow into the expansion chamber 305 through the pressure discharging hole 306. The internal air pressure of the expansion chamber 305 increases with the increase of the heating temperature, and the pressurized gas is released through the above pressure discharging hole 306 to prevent the heating device 300 itself from being thermally expanded and damaged.

The heating device 300 further includes an electrode part 302 connected to the heating element 304. The electrode part 302 generally includes a positive electrode and a negative electrode. At the time of packaging, at least a portion of the two electrode parts 302 protrudes to the outside of the quartz glass body 303 for being connected to the power supply. In the present embodiment, the electrode part 302 uses a wire or is an electrode component suitable for electrical contact.

Unlike the solid tobacco material, a drainage mechanism is required for heating the tobacco liquid to cooperate with the heating device. Therefore, in addition to the heating device 300, the atomizing device 200 further includes a porous member 202 and a support 201 for fixing and supporting the porous member 202 and the heating device 300. The porous member 202 and the heating device 300 are mounted inside the support 201. Air flow may enter through the bottom of the support 201. The top of the support 201 is provided with an outlet through which air flow and aerosol are discharged. A screw thread is provided outside the support 201, which is configured for being mounted inside the housing 101.

The porous member 202 has a microporous structure therein for slowly conveying the tobacco liquid from the storage chamber 102 onto the quartz glass body 303 of the heating device 300. The porous member 202 is in contact with at least a part of the outer surface of the quartz glass body 303. The tobacco liquid absorbed by the porous member 202 is conducted to the surface of the quartz glass body 303 and heated and atomized.

The porous member 202 can be made of a material such as a microporous ceramic body, a fiber cotton, or a foam metal. In the present embodiment, the porous member 202 preferably adopts a cylindrical microporous ceramic body 2021. Since the microporous ceramic body 2021 is made of a hard material, a layer of fiber cotton 2022 is also wrapped around the periphery of the microporous ceramic body 2021 in order to prevent the poor contact between the microporous ceramic body 2021 and the inner wall of the support 201 from generating a leakage of tobacco liquid. That is to say, the porous member in the present embodiment preferably uses a combination of the microporous ceramic body 2021 and the fiber cotton 2022. The heating device 300 is located inside of the microporous ceramic body 2021.

The porous member 202 and the quartz glass body 303 are both disposed along an axial direction of the aerosol discharging channel 303, the porous member 202 and the quartz glass body 303 cooperatively define an air flow channel therebetween, and the air flow channel is in communication with the aerosol discharging channel 303 to facilitate the aerosol formed by evaporating the tobacco liquid on the porous member 202 to be smoothly discharged into the aerosol discharging channel 103.

Figure 4:
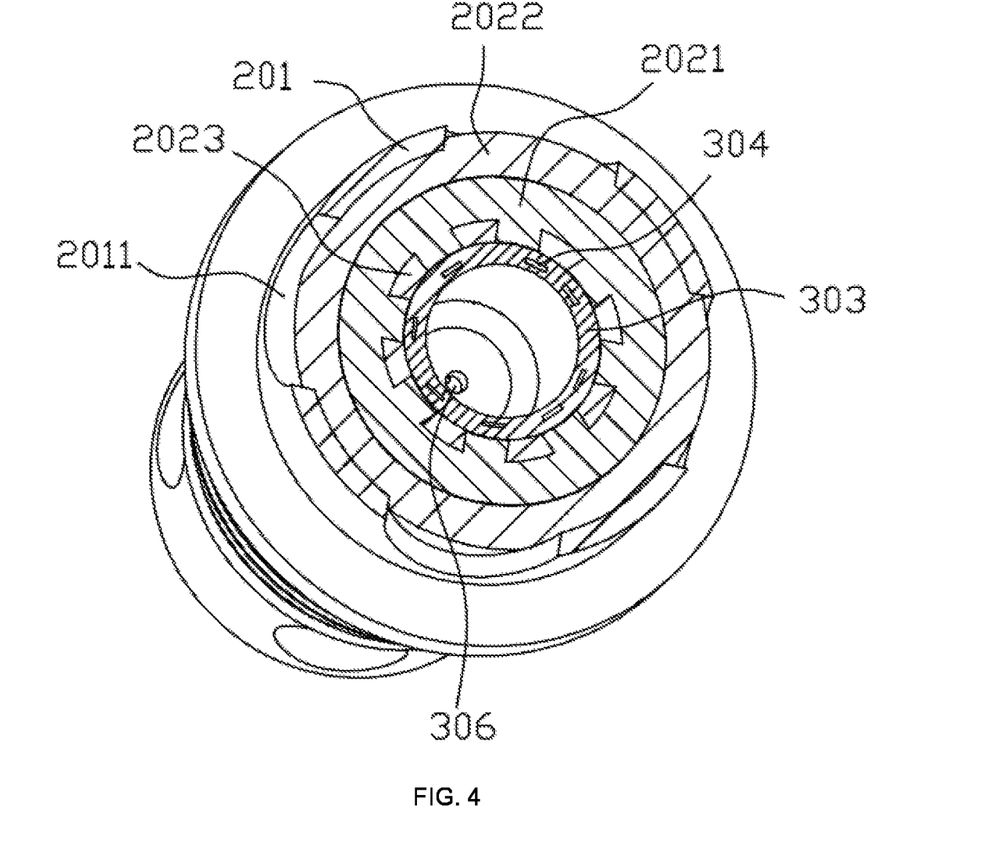
FIG. 4 is a cross-sectional view of an atomizing device according to a first embodiment.
Figure 5:
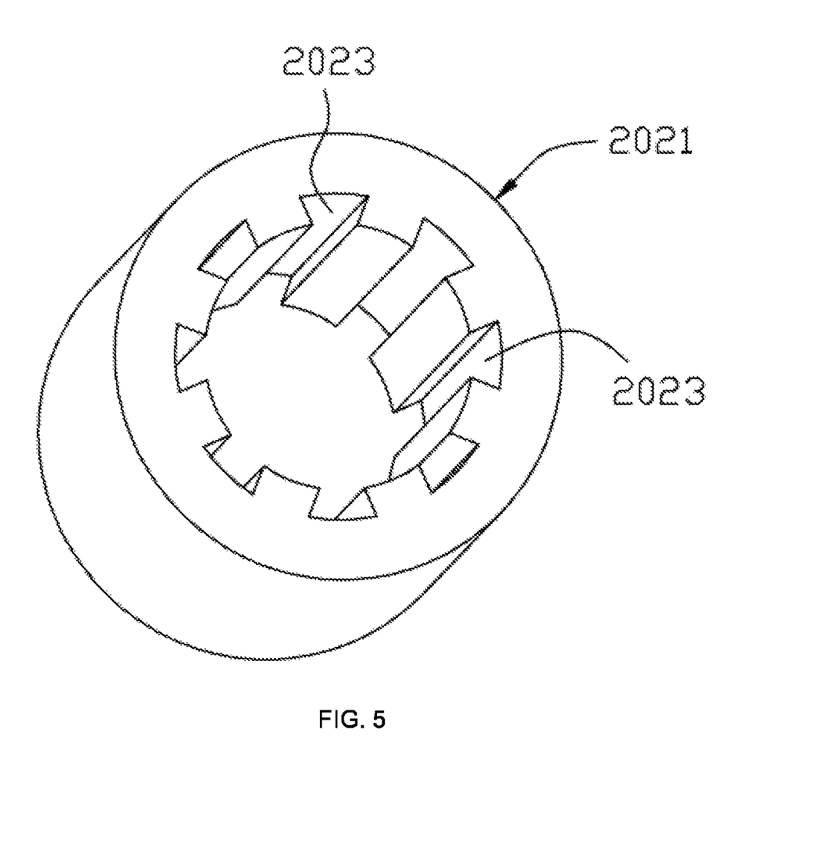
FIG. 5 is a schematic structural view of a porous member with an air flow groove according to a first embodiment.

Referring to FIG. 4 and FIG. 5, as a preferred mode of the present embodiment, a porous member 202 (composed of a microporous ceramic body 2021 and a fiber cotton 2022) is disposed around the periphery of the quartz glass body 303, the porous member 2021 defines a plurality of axially extending air flow grooves 2023 in the inner wall, the air flow grooves 2023 runs through the entire microporous ceramic body 2021, and the air flow grooves 2023 and the outer wall of the quartz glass body 303 cooperate to form the above air flow channel. A plurality of air flow grooves 2023 are circumferentially distributed, and a plurality of protruding arms in contact with the quartz glass body 303 are provided between the adjacent air flow grooves 2023 for conveying the tobacco liquid. The air flow grooves 2023 has an effect that the air flow passes therethrough and has another effect that the evaporation area of the tobacco liquid is increased. The tobacco liquid conveyed from the inner wall of the air flow groove 2023 is heated by the heat radiation and infrared radiation to generate aerosol, which is discharged into the air flow groove 2023.

When the atomizing device 200 is mounted in the storage chamber 102 of the aerosol generator 100, the periphery of the support 201 is surrounded by the tobacco liquid. In order to allow the tobacco liquid to flow into the porous member 202, a liquid guiding hole 2011 is defined on the side wall of the support 201, through which the tobacco liquid in the storage chamber 102 flows to the porous member 202. The tobacco liquid is absorbed by the fiber cotton 2022 through the liquid guiding holes 2011, and is conveyed to the heating device 200 through the microporous ceramic body 2021. A fixing net 203 is further provided above the inner part of the support 201 for pressing the fiber cotton 2022 to prevent its dislocation movement.

In the present embodiment, the quartz glass body 303 is substantially cylindrical. The quartz glass body 303 includes a tapered portion 301 at the top thereof. A part of the tobacco liquid in the aerosol discharging channel 103 condenses to form a liquid droplet and flows back downwards in the cold environment. The tapered portion 301 may allow the liquid droplet flowing back to smoothly flow into the air flow channel (i.e., the air flow groove 2023) of the heating device 300 and is atomized again.

Referring to FIG. 1 again, an isolating cover body 104 and a spring 105 are movably disposed in the storage chamber 102, the isolating cover body 104 and the spring 105 are located at the periphery of the porous element 202 and the heating device 300, and a suction nozzle cover 106 screwed to the isolating cover body 104 is further mounted on the housing 101. When the suction nozzle cover 106 is unscrewed, the isolating cover body 104 is moved downward upon a pushing force of the spring 105 and covers the entire atomizing device 200 to isolate the tobacco liquid from flowing into the porous element 202. In this state, the tobacco liquid may be added into the storage chamber 102 through the upper opening, and the tobacco liquid will not leak from the atomizing device 200 when the liquid is filled; and when the suction nozzle cover 106 is screwed, the isolating cover body 104 moves upward to allow the porous member 202 to come into contact with the tobacco liquid due to the screwing force of the screw thread, and the atomizing device 200 may work normally.

A Second Embodiment

The present embodiment also provides an aerosol generator, the overall structure of which is similar to that of the first embodiment, except that the atomizing device 400 therein is different from the atomizing device 200 in the first embodiment 1 in structure.

Figure 6:
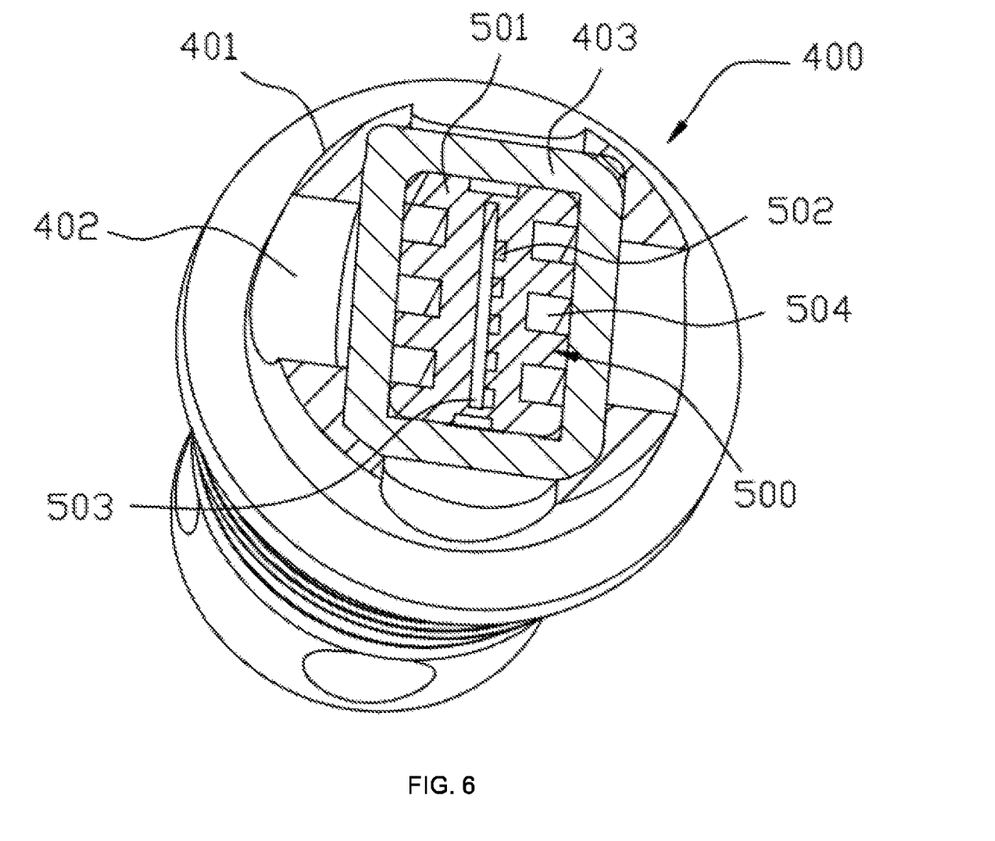
FIG. 6 is a cross-sectional view of an atomizing device according to a second embodiment.
Figure 7:
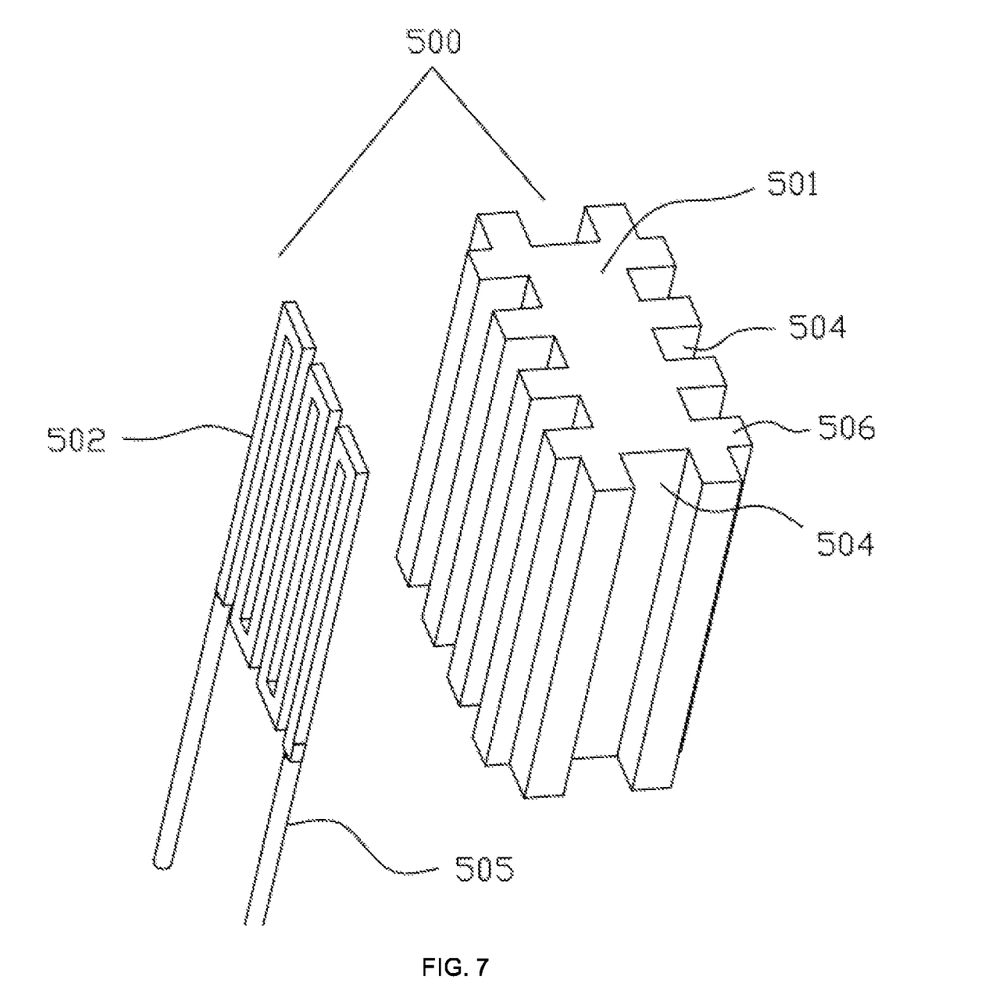
FIG. 7 is an exploded schematic view of a heating device provided in a second embodiment.

As shown in FIG. 6 and FIG. 7, the atomizing device 400 includes an outer support 401, an inner heating device 500 and a porous member 403 surrounding the periphery of the heating device 500. A plurality of liquid guiding hole 402 are defined on the side wall of the support 401. The heating device 500 includes a quartz glass body 501 and a heating element 502 embedded in the quartz glass body 501. The heating element 502 is a metal electric heating element. Electrode parts 505 are connected to both ends of the heating element 502, respectively. Similarly, an expansion chamber 503 and a pressure discharging hole are defined at the position in the quartz glass body 501 near the heating element 502.

In the present embodiment, the porous member 403 is made of flexible fiber cotton. The fiber cotton is disposed around the periphery of the quartz glass body 501. The quartz glass body 501 defines a plurality of axially extending air flow grooves 504 in the outer wall, the air flow grooves are circumferentially spaced along the outer wall of the quartz glass body 501, the air flow grooves 504 are uniformly surrounded, and the air flow grooves 504 and the inner wall of the porous member 403 cooperate to form the air flow channel, through which the air flow passes. A plurality of heating arms 506 are spaced between the adjacent air flow grooves 504. Each of the plurality of heating arms 506 is in contact with the fiber cotton to heat the tobacco liquid provided by the fiber cotton.

Preferably, in the present embodiment, the outer shape of the quartz glass body 501 of the heating device 500 is substantially square or cylindrical as in the first embodiment. In addition to the cylindrical shape and the square shape provided in the above two embodiments, the outer shape of the quartz glass body is of a sheet shape or other shapes. For example, when a sheet shape is used, the heating sheet is also embedded in the quartz glass body, the porous member is provided between the quartz glass body and the liquid outlet of the storage chamber, and the sheet-shaped quartz glass body is directly attached to the surface of one of the porous members which may convey the tobacco liquid.

A Third Embodiment

Figure 8:
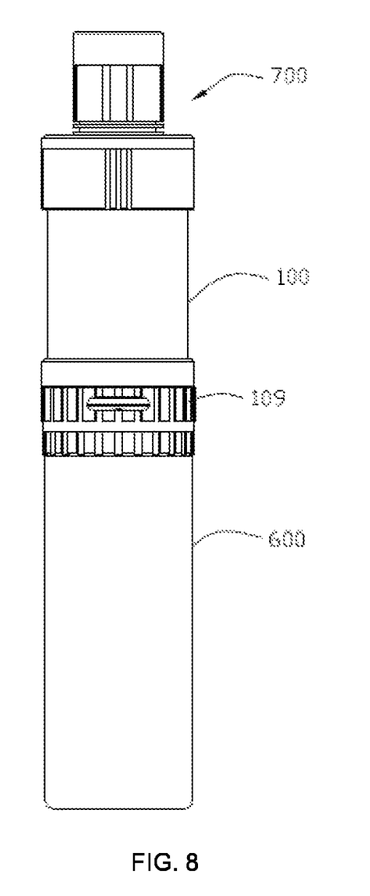
FIG. 8 is a schematic view of an electronic cigarette provided in a third embodiment.

As shown in FIG. 8, the present embodiment provides an electronic cigarette 700, which includes an aerosol generator 100 and a power supply 600, both of which are detachably connected. The aerosol generator 100 is described in the first embodiment, and the power generator 600 is electrically connected to the heating element 304 in the heating device 300. It is to be understood that the aerosol generator, the atomizing device 400, and the heating device 500 provided in the second embodiment may all be applied to the electronic cigarette 700 of the present embodiment.

It should be noted that the aerosol generator and the power supply device in the electronic cigarette provided by the present invention are not necessarily of a split-type structure. For example, when the aerosol forming substance is solid tobacco, the power supply device may also be directly mounted inside the aerosol generator to form an integrated structure.

The above embodiments are only some embodiments of the present specification listed for the sake of easy understanding of the summary of the present invention, and are not intended to limit the technical solutions of the present invention, and not intended to be exhaustive of any possible implementation. Therefore, any minor improvements or equivalent substitutions made to the structures, the flows, or the steps of the present invention should be included in its scope of protection.

What is claimed is:

1. An aerosol generator, comprising:
   a housing;
   a storage chamber formed in the housing and configured for storing an aerosol forming substance;
   a heating device disposed in the housing and configured to heat the aerosol forming substance to generate aerosol; and
   an aerosol discharging channel configured for discharging aerosol generated by the aerosol forming substance to the outside of the housing;
   wherein the heating device comprises a quartz glass body and a heating element, the heating element is encapsulated inside the quartz glass body, and the heating element is capable of generating thermal radiation and infrared radiation outwardly through the quartz glass body to heat the aerosol forming substance;
   wherein an expansion chamber is formed inside the quartz glass body during the encapsulating process, and a pressure discharging hole is provided in the quartz glass body to allow the expansion chamber to communicate with the outside.

2. An electronic cigarette, comprising an aerosol generator and a power supply device, wherein the aerosol generator is the aerosol generator according to claim 1, and the power supply device is electrically connected with the heating element of the heating device.

3. The aerosol generator according to claim 1, wherein the heating device further comprises an electrode part connected to the heating element, and at least a part of the electrode part protrudes to the outside of the quartz glass body.

4. The aerosol generator according to claim 1, wherein the heating element is an electric heating sheet, an electric heating wire or an electric heating net embedded in the quartz glass body.

5. The aerosol generator according to claim 1, wherein the aerosol forming substance is solid tobacco material or tobacco liquid in a fluid form.

6. The aerosol generator according to claim 5, wherein when the aerosol forming substance is tobacco liquid, the aerosol generator further comprises a porous member, the porous member is configured for slowly conveying the tobacco liquid from the storage chamber to the heating device, and the porous member is in contact with the outer surface of the quartz glass body.

7. The aerosol generator according to claim 6, wherein the porous member is a microporous ceramic body, a fiber cotton, or a foam metal.

8. The aerosol generator according to claim 6, wherein both the porous member and the quartz glass body are disposed along an axial direction of the aerosol discharging channel, the porous member and the quartz glass body cooperatively define an air flow channel therebetween, and the air flow channel is in communication with the aerosol discharging channel.

9. The aerosol generator according to claim 8, wherein the porous member is disposed around the periphery of the quartz glass body, the porous member defines a plurality of axially extending air flow grooves in the inner wall, and the air flow grooves and the outer wall of the quartz glass body cooperate to form the air flow channel.

10. The aerosol generator according to claim 8, wherein the porous member is disposed around the periphery of the quartz glass body, the quartz glass body defines a plurality of axially extending air flow grooves in the outer wall, the air flow grooves are circumferentially spaced along the outer wall of the quartz glass body, and the air flow grooves and the inner wall of the porous member cooperate to form the air flow channel.

11. The aerosol generator according to claim 8, further comprising a support for fixing the porous member and the heating device outside the porous member, wherein a liquid guiding hole is defined on the side wall of the support, through which the tobacco liquid in the storage chamber flows to the porous member.

12. The aerosol generator according to claim 9, further comprising a support for fixing the porous member and the heating device outside the porous member, wherein a liquid guiding hole is defined on the side wall of the support, through which the tobacco liquid in the storage chamber flows to the porous member.

13. The aerosol generator according to claim 10, further comprising a support for fixing the porous member and the heating device outside the porous member, wherein a liquid guiding hole is defined on the side wall of the support, through which the tobacco liquid in the storage chamber flows to the porous member.

14. The aerosol generator according to claim 8, wherein the quartz glass body comprises a tapered portion at the top thereof.

15. The aerosol generator according to claim 6, further comprising an isolating cover body and a spring located at the periphery of the porous element and the heating device, wherein the isolating cover body and the spring are movably disposed in the storage chamber, and a suction nozzle cover screwed to the isolating cover body is further mounted on the housing; when the suction nozzle cover is unscrewed, the isolating cover body moves downward under the action of the spring to isolate the tobacco liquid from flowing into the porous element, and when the suction nozzle cover is screwed, the isolating cover body moves upward to allow the porous member to come into contact with the tobacco liquid.

16. The aerosol generator according to claim 6, wherein an air inlet is defined downstream of the heating device, the aerosol generator further comprises an adjusting ring mounted at the position of the housing corresponding to the air inlet, and the adjusting ring is configured for adjusting the size of the air inlet.

17. The aerosol generator according to claim 1, wherein the quartz glass body has a cylindrical shape, a square shape or a sheet shape.

18. An atomizing device detachably mounted inside an aerosol generator, comprising:
   a heating device configured for heating tobacco liquid to evaporate and generate aerosol, wherein the heating device comprises a quartz glass body and a heating element, the heating element is encapsulated inside the quartz glass body, and the heating element is capable of generating thermal radiation and infrared radiation outwardly through the quartz glass body to heat the tobacco liquid;
   a porous member in contact with the quartz glass body of the heating device and configured for absorbing and conducting the tobacco liquid to the heating device; and
   a support disposed on the periphery of the heating device and the porous member, the support being configured for fixing the heating device and the porous member.

* * * * *